United States Patent [19]

England et al.

[11] Patent Number: 4,608,206
[45] Date of Patent: Aug. 26, 1986

[54] FLUORINATED 3-KETOGLUTAROYL HALIDES

[75] Inventors: David C. England, Wilmington; Edward G. Howard, Jr., Hockessin, both of Del.

[73] Assignee: E. I. Du Pont de Nemours and Company, Wilmington, Del.

[21] Appl. No.: 277,662

[22] Filed: Jun. 26, 1981

Related U.S. Application Data

[62] Division of Ser. No. 95,071, Nov. 16, 1979, Pat. No. 4,299,949.

[51] Int. Cl.$^4$ .................. C07C 51/58; C07C 55/40
[52] U.S. Cl. .............................. 260/544 F; 260/544 Y
[58] Field of Search .................. 260/544 F, 544 Y

[56]  References Cited

U.S. PATENT DOCUMENTS

| | | | |
|---|---|---|---|
| 2,988,537 | 6/1961 | Wiley | 528/244 |
| 3,342,777 | 9/1967 | Howard | 528/220 |
| 4,138,426 | 2/1979 | England | 560/184 |
| 4,160,780 | 7/1979 | Krespan | 260/513 F |
| 4,169,934 | 10/1979 | Papanu | 525/418 |
| 4,275,225 | 6/1981 | Krespan | 560/174 |
| 4,304,927 | 12/1981 | Krespan | 560/184 |

OTHER PUBLICATIONS

England et al., J. of Fluorine Chemistry 3, 63 (1973–1974).
McBee et al., J. Am. Chem. Soc. 75, 3152 (1953) and 75, 4090 (1953).

*Primary Examiner*—Natalie Trousof
*Assistant Examiner*—L. Hendriksen
*Attorney, Agent, or Firm*—James A. Costello

[57]  ABSTRACT

Compounds having the formula:

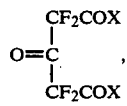

where X is F or Cl, and a process for the preparation of such compounds.

2 Claims, No Drawings

FLUORINATED 3-KETOGLUTAROYL HALIDES

CROSS-REFERENCE TO RELATED APPLICATION

This is a division of U.S. application Ser. No. 095,071 filed on Nov. 16, 1979, now U.S. Pat. No. 4,299,949.

BACKGROUND OF THE INVENTION

1. Field of the Invention

This invention relates to certain fluorinated acid halides of 3-ketoglutaric acid.

2. Relation to Prior Art

Copolymers of ethylenically unsaturated compounds and polyfluoroketones of the type

are disclosed in U.S. Pat. No. 3,342,777 to Howard, where X and X', independently, may include F, Cl, perfluoroalkyl, ω-halo- and ω-alkoxy-perfluoroalkyl substituents.

Ketodiethers of the type, ROCF$_2$CF$_2$C(O)CF$_2$CF$_2$OR, are known in U.S. Pat. No. 2,988,537, as is the hydrolysis of —CF$_2$OR groups to —CO$_2$R, and the conversion of ether groups —CF$_2$OCH$_3$ to —COF by the action of SO$_3$, D. C. England et al, J. of Fluorine Chemistry 3, 63 (1973-74). Ketomonoesters of the type

(R=H, C$_2$H$_5$), and their preparation by reacting a difluoroacetate with a trifluoroacetate, are also known, McBee et al, J. Am. Chem. Soc. 75, 3152 (1953) and 75, 4090 (1953).

SUMMARY OF THE INVENTION

This invention comprises fluorinated ketones having the formula O=C(CF$_2$COX)$_2$ where X is F or Cl, copolymers of these ketones which contain the chain segment

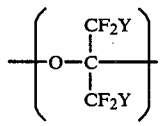

where Y is —COOR; R is H, alkyl of 1 to 8 carbon atoms, cycloalkyl of 7 to 8 carbon atoms, phenyl, alkaryl of 7 to 8 carbon atoms, an alkali metal, a metal of Group IIA or IIB, ammonium, or quaternary ammonium; —COF, —COCl, —CN, —CONH$_2$, —CONHR$^1$ where R$^1$ is alkyl of 1 to 8 carbon atoms, cycloalkyl of 7 to 8 carbon atoms, phenyl, alkaryl of 7 to 8 carbon atoms, —CH$_2$NH$_2$, —CH$_2$OH. Many of these copolymers are obtained by reacting the copolymer containing the acid halide group with another compound. The copolymers of the invention are useful for providing cure sites in elastomeric compositions, as metal protective coatings, and in ionizable —COOH or —COOM forms, as electrically conductive and water-wettable, dyeable resins.

DETAILS OF THE INVENTION

The fluorinated monomers of this invention are derivatives of 3-ketoglutaric acid and have the formula O=C(CF$_2$COX)$_2$ where X is F or Cl. These compounds are prepared by reacting bis(2-alkoxytetrafluoroethyl) ketones with sulfur trioxide:

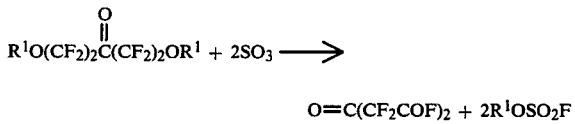

where R$^1$ is, independently, H, CH$_3$, C$_2$H$_5$, CH$_2$CH$_2$CH$_3$ or CH$_2$CH$_2$CH$_2$CH$_3$. Tetrafluoro 3-ketoglutaroyl fluoride may be converted to the corresponding acid chloride by passage, in vapor form, over solid calcium chloride

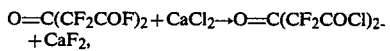

and to diesters by alcoholysis

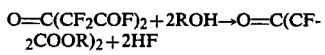

Such diesters can also be prepared by contacting bis(2-alkoxytetrafluoroethyl) ketones with strong protic acids such as concentrated sulfuric acid, as described in U.S. application Ser. No. 850,593, now U.S. Pat. No. 4,304,927:

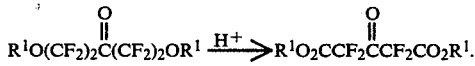

Generally a mixture of 1–4 parts of concentrated sulfuric acid and 1 part of fluoroether are allowed to react until exothermic reaction is complete; the product is isolated by distillation.

Bis(2-alkoxytetrafluoroethyl) ketones are prepared from tetrafluoroethylene, a dialkyl carbonate and a metal alkoxide as described in U.S. Pat. No. 2,988,537 (Wiley)

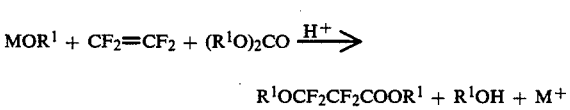

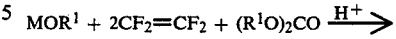

where R$^1$ is, independently, as defined above. Normally the above reactions proceed concurrently, producing a mixture of compounds. The ketone may be separated, e.g. by distillation, from the ester product before reaction with SO$_3$. However, it has been found that the yield of perfluoro-3-ketoglutaroyl fluoride is actually improved if a mixture of compounds as produced in the above reactions is reacted with SO$_3$.

Preparation of mixture of compounds requires the addition of one or two moles of tetrafluoroethylene to a mixture of one mole of alkali metal alkoxide and one mole of a dialkyl carbonate in a dry (moisture-free), inert solvent such as tetrahydrofuran, diethyl ether, 1,2-dimethoxy ethane and the like. Alkoxides of sodium are preferred, though other alkali metals are also functional. Suitable alkoxides are those of straight chain aliphatic alcohols of up to seven carbon atoms, particularly the alkoxides of shorter chain alkanols of from 1 to 4 carbon atoms such as methanol, ethanol, n-propanol and n-butanol.

Carbonate esters useful in the synthesis of the mixture of compounds are those of straight chain aliphatic alcohols of up to seven carbon atoms, preferably those of alkanols of from 1 to 4 carbon atoms.

The reaction of $SO_3$ with bis(2-alkoxytetrafluoroethyl) ketones or mixtures thereof with 3-alkoxytetrafluoropropionates is normally carried out using 1 to 10 mols of $SO_3$, preferably 1.5 to 4 mols of $SO_3$ per equivalent of —$CF_2OCH_3$ groups in the ketone or ketone/propionate mixture. Reaction temperatures may be about 25° to about 150° C., preferably 40° to 100° C.

Ketones of this invention, $O=C(CF_2COX)_2$, undergo free radical initiated colymerization by the method described in U.S. Pat. No. 3,342,777 (Howard) with one or more ethylenic compounds selected from among the following: tetrafluoroethylene, chlorotrifluoroethylene, 1,1-dichlorodifluoroethylene, vinylidene fluoride, vinyl fluoride, trifluoroethylene, ethylene, hexafluoropropylene, perfluoromethylvinyl ether, bromotrifluoroethylene, methyl acrylate, methyl methacrylate, vinyl acetate and acrylonitrile.

Copolymerization of these formula ketones with one or more ethylenic comonomers, is initiated by free radicals derived from any suitable source, particularly organic peroxides such as perfluoropropionyl peroxide, benzoyl peroxides, persulfates or azonitriles. Perfluoropropionyl peroxide is a preferred initiator. Initiator concentration is determined by the nature of the initiator used, the nature and reactivity of the comonomers, and the desired polymer molecular weight. Perfluoropropionyl peroxide is normally used at concentrations of about 0.01 to 1 mol %, preferably 0.05 to 0.3 mol %. Reaction is carried out in an oxygen-free atmosphere, with either an inert solvent such as 1,2,2,-trichloroethane or 1,2,2-trichloro-1,1,2-trifluoroethane or without added solvent, at pressures and temperatures determined by the nature and reactivity of the comonomers and the desired product composition. A pressure reactor is used with low-boiling monomers.

The present invention also includes the copolymers obtained by polymerizing the ketones containing side chain acid halide functions with ethylenic compounds. Such copolymers consist essentially of recurring units of at least one ethylenic compound in a ratio of about 1:1 to about 20:1 to recurring units of $$-O-\underset{\underset{CF_2COX}{|}}{\overset{\overset{CF_2COX}{|}}{C}}-$$

where X is defined as above.

Acid halide functions in the polymers of this invention may be partially or completely hydrolyzed by water or aqueous alkali to carboxylic acid groups; e.g.

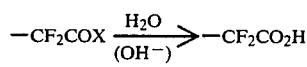

The acid halide functions may also be converted by alcoholysis into ester functions

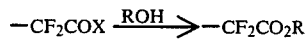

Use of polyhydric alcohols, such as ethylene glycol, results in cross-linked, intractable structures (Example 7). Some or all of the side chain —COOH groups or acid halide groups may be converted, by known methods, to derivative functions. Thus, the present invention provides novel copolymers which contain within the polymer chain segments of

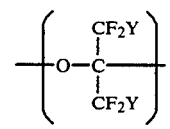

where Y is —COOR (R=H, alkyl of 1 to 8 carbon atoms, cycloalkyl to 8 carbon atoms, phenyl, alkaryl of 7 to 8 carbon atoms, an alkali metal, a metal of Group IIA or IIB, ammonium or quaternary ammonium), —COF, —COCl, —CONH$_1$, —CONHR$^1$, where R$^1$ is alkyl of 1 to 8 carbon atoms, cycloalkyl of 7 to 8 carbon atoms, phenyl, alkaryl of 7 to 8 carbon atoms, —CH$_2$NH$_2$, —CH$_2$OH, or —CN.

The carboxylate salts (R=M) are obtained by treating the polymer in its —COOH or —CO$_2$R forms with alkali metal or Group IIA or IIB metal hydroxides, carbonates, or salts of organic acids such as acetates, formates and the like; ammonium hydroxide or quaternary ammonium hydroxide.

Primary amide functions (—CONH$_2$) are introduced by reacting the polymer in its acid halide or carboxylic ester form with concentrated aqueous or gaseous ammonia, e.g.

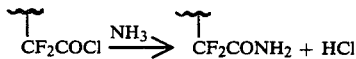

Substituted amide functions (—CONHR$^1$) are introduced by reacting the polymer in its acid halide form with a primary amine, e.g.

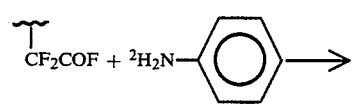

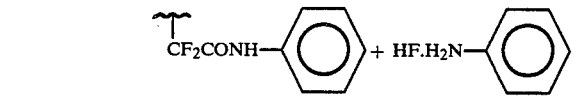

Amine (—CH$_2$NH$_2$) and alcohol (—CH$_2$OH) functions can be introduced by catalytic hydrogenation of the amide or nitrile, and ester forms respectively; lithium aluminum hydride is a suitable reagent. Nitrile (—CN) functions are introduced by the dehydration of the amide (—CONH$_2$) groups with a suitable dehydrating agent such as $P_2O_5$ or $POCl_3$. Procedures for carrying out the above conversions are described in organo-fluorine chemistry texts including Lovelace, Rausch & Postelnek "Aliphatic Fluorine Compounds", Reinhold Book Corp. (1958).

The polymers of this invention, depending on the choice of side chain functionality, are useful as curing agents for elastomeric compositions, water wettable dye sites for catonic dyes, metal protective coatings, ion-conductive materials; all are suitable for conversion to films and fibers. Polymers in the form of acid salts, particularly the carboxylates of $Zn^{++}$ and $Mg^{++}$, are unusually tough, strong thermoplastic materials (Example 13).

SPECIFIC EMBODIMENTS OF THE INVENTION

The following examples illustrate ways of carrying out the present invention. All parts and percentages are by weight unless otherwise stated.

EXAMPLE 1

Preparation of 3-Ketotetrafluoroglutaroyl Fluoride $$CH_3OCF_2CF_2COOCH_3 + SO_3 \longrightarrow$$
$$\underset{\sim}{1^*}$$

$$FOCCF_2COOCH_3 + CH_3OSO_2F$$
$$\underset{\sim}{4}$$

$$CH_3OCF_2CF_2COCF_2CF_2OCH_3 + 2SO_3 \longrightarrow$$
$$\underset{\sim}{2^{**}}$$

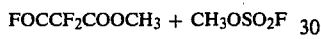

$$O = C(CF_2COF)_2 + 2CH_3OSO_2F$$
$$\underset{\sim}{3}$$

A mixture (200 g, 1.20 equivalents of 1 (65%) and 2 (35%)) above prepared by the reaction of tetrafluoroethylene with dimethyl carbonate was added dropwise with stirring to 80 ml (1.91 mol) of sulfur trioxide in a pot attached to a still. The rate of addition was controlled to maintain a gentle reflux and when complete, the pot was heated to distill the contents. There was collected: 27 g (50%) of 3, b.p. 54° and 77 g (70%) of 4, b.p. 82°. Compound 3 codistilled with a little $SO_3$ and 4 with about an equal amount of the by-product methyl fluorosulfate. These contaminants were removed by passing the mixture over sodium fluoride pellets at 400°/1 to 5 mm.

Compound 3 absorbed in the infrared at 1900 cm$^{-1}$ (C=O). The $^{19}F$ NMR spectrum was obtained with a Varian A56/60 spectrometer operating at 56.4 MHz; chemical shifts are in ppm downfield from $CFCl_3$ as internal standard: 20.3 ppm (multiplet, 2F) and −113.8 (multiplet, 4F). Elemental analysis was consistent with the formula $C_5F_6O_3$.

EXAMPLE 2

Preparation of 3-Ketotetrafluoroglutaroyl Fluoride $$CH_3OCF_2CF_2COCF_2CF_2OCH_3 + 2SO_3 \longrightarrow$$
$$\underset{\sim}{2}$$

-continued $$O = C(CF_2COF)_2 + 2CH_3OSO_2F$$
$$\underset{\sim}{3}$$

$$CH_3OCF_2CF_2CO_2CH_3 + SO_3 \longrightarrow$$
$$\underset{\sim}{1}$$

$$FOCCF_2COOCH_3 + CH_2OSO_2F$$
$$\underset{\sim}{4}$$

Sulfur trioxide (100 ml, 191 g, 2.39 mol) was magnetically stirred in a round-bottom flask fitted with a dropping funnel and reflux condenser. A mixture (135 g, 0.898 equivalents of 1 (24%) and 2 (76%)) was added at a rate to maintain a gentle reflux. When addition was complete, the dropping funnel was replaced with a short still head and material boiling up to 80° was collected. This material was then washed with concentrated sulfuric acid to remove excess sulfur trioxide, and then redistilled, b.p. 54°, yield, 53 g (67.5%).

EXAMPLE 3

Copolymers of 3-Ketotetrafluoroglutaroyl Fluoride and Vinylidene Fluoride

A copolymer having the following formula was prepared:

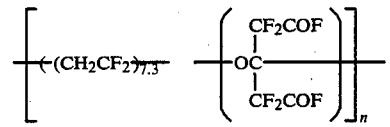

A stainless steel shaker tube, dry and oxygen free was charged with a nitrogen-purged solution consisting of 25 g $OC(CF_2COF)_2$ (0.11 mol), 30 ml of 1,1,2-trichloro-trifluoroethane ($Cl_2CFCF_2Cl$) and 0.3 g perfluoropropionyl peroxide as a 10% solution in $Cl_2CFCF_2Cl$. After adding 40 g $CH_2=CF_2$ (0.67 mol), the closed reactor was shaken at 35° C. The temperature suddenly increased to 56° C. momentarily and the polymerization was resumed at 30°–38° C. for a total of 20 hrs. The product was stirred with boiling water to remove solvent, excess monomers, and to hydrolyze the acid fluoride group to carboxylic acid. The dried product (37 g) was hot pressed at 200° C. to a transparent easily stretched strong film. Elemental analysis was consistent with the above formula.

Neutral equivalent, at 683 and 341.

Infrared, strong C=O at 1750 cm$^{-1}$; strong C—F at 1250–1110 cm$^{-1}$; OH, 3770 cm$^{-1}$.

The polymer was very soluble in acetone from which a film was cast. The film had these physical properties (6 samples):

Tensile (max) 1674±16 psi.
Yield Elongation 19%.
Modulus, 40, 964±2353 psi.
The carbonyl band strength of hot pressed film was 108 absorbency %/mil.

EXAMPLE 4

Copolymer of 3-Ketotetrafluoroglutaroyl Fluoride and Ethylene

As in Example 3, a shaker tube was charged with 14 g OC(CF$_2$COF)$_2$ and 0.3 g benzoyl peroxide. The mixture was copolymerized with ethylene at 85° C. under 300 atm ethylene pressure for 2 hours and under 500 atm ethylene pressure for 7 hours. The total ethylene pressure drop during polymerization was 40 atm. The product was treated with boiling water for 2 hours to hydrolyze acid fluoride functions and dried at 110° C. under 0.5 mm pressure for one hour. The product (4 g) was soluble in aqueous sodium bicarbonate. Neutral equivalent was 153. Elemental analysis was consistent with the formula:

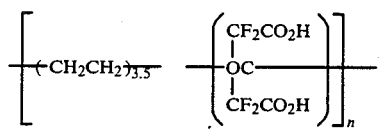

An infrared spectrum of a film hot pressed between NaCl plates, had the following absorptions in keeping with the above structure:
Strong broad OH (for CO$_2$H) at 3230–3125 cm$^{-1}$.
Strong C—H 1725 cm$^{-1}$.
C—F and C—O 1250–1150 cm$^{-1}$.
C=O at 1725 cm$^{-1}$.

EXAMPLE 5

Copolymer of 3-Ketotetrafluoroglutoroyl Fluoride and Tetrafluoroethylene

A shaker tube was charged with 25 g (0.11 mole) OC(CF$_2$COF)$_2$, 0.3 g perfluoropropionyl peroxide and 40 g (0.4 mol) tetrafluoroethylene. Polymerization was exothermic and the temperature rose to 53° C. where the pressure was 192 psi; when cooled to 35° C., the pressure dropped to 150 psi; after 35 minutes the pressure was 60 psi, and after a further 9 hours the pressure had declined to 21 psi. The air dried product was treaded with boiling water for 3 hours to hydrolyze acid fluoride functions, and dried at 110° C. under 0.5 m for 3 hours; 36 g. A translucent film pressed at 100° C. (polymer was *not* fused) had, in addition to C—F infrared absorption, broad OH of a COOH group at 3100–3700 cm$^{-1}$ and C=O band at 1780 cm$^{-1}$ equal to 7.6 absorbency %/mil.

EXAMPLE 6

Copolymer of 1,5-Dimethyl-3-Ketotetrafluoroglutarate and Vinylidene Fluoride

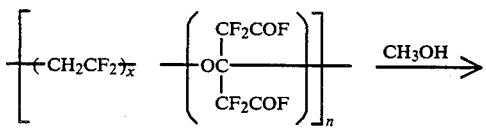

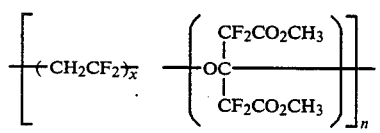

The procedure described in Example 3 was followed using 22 g of OC(CF$_2$COF)$_2$, 0.15 g of perfluoropropionyl peroxide and 50 ml of Cl$_2$CFCF$_2$Cl as solvent. The mixture was heated at 35° C. for 17 hrs under a pressure of vinylidene fluoride; initial pressure was 165 psi; final pressure 120 psi. A portion of the polymeric product was steeped in 100 ml of methanol for 2 days at room temperature. An exothermic reaction occurred with liberation of HF. The polymer product was filtered and dried at 110° C. under vacuum (0.5 mm Hg) for 3 hrs. Hot pressing at 190° C. gave a very strong, slightly elastomeric film. IR: v. weak band at 3650 cm$^{-1}$ (carboxyl —OH); strong, single carbonyl band at 1770 cm$^{-1}$.

Copolymers of 1,5 dimethyl-3-ketotetrafluoroglutarate and vinylidene fluoride can also be prepared by directly polymerizing these two monomers under similar conditions. Copolymers obtained directly or by means of esterification of the acid halide can be further reacted if desired, for example, hydrolyzed to acid groups, and converted to salt groups—see Example 11.

EXAMPLE 7

A portion of the vinylidene fluoride/3-ketoglutaroyl fluoride copolymer prepared in Example 6 was steeped in ethylene glycol at 60° C. for 3 hrs. An exothermic reaction occurred with liberation of HF. The polymer obtained after filtering and drying as in Example 6 would not melt flow, indicating a crosslinked structure resulting from glycolate formation of the type:

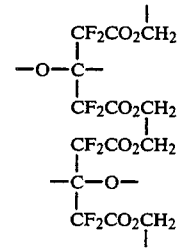

EXAMPLE 8

Copolymer of 3-Ketotetrafluoroglutaroyl Fluoride, Tetrafluoroethylene and Ethylene

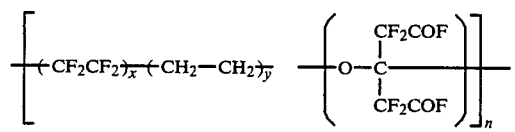

The procedure of Example 3 was repeated using 4 g of OC(CF$_2$COF)$_2$, 0.2 g of perfluoropropionyl peroxide, 40 g of tetrafluoroethylene, 11 g of ethylene and 50 ml of Cl$_2$CFCF$_2$Cl as solvent. Polymerization was continued for 10 hours at 35°–42° C.; initial pressure was 3.5 psi, final pressure 78 psi. The polymer product was hydrolyzed in boiling water for 3 hours to convert —COF groups to —COOH, and dried. Yield, 42 g. A film, pressed as in Example 3, was brittle. IR:, strong absorption at 2800–3500 cm$^{-1}$ (OH from —COOH); C=O absorbency 23%/mil.

EXAMPLE 9

Copolymer of 3-Ketotetrafluoroglutaroyl Fluoride, Tetrafluoroethylene and Vinylidene Fluoride

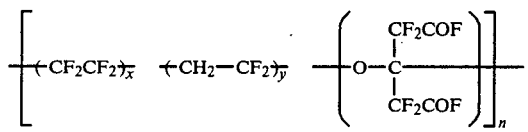

The procedure of Example 3 was repeated using 22 g of $OC(CF_2COF)_2$, 0.1 g of perfluoropropionyl peroxide, 25 g of tetrafluoroethylene, 16 g of vinylidene fluoride and 40 ml of $Cl_2CFCF_2Cl$ as solvent. Polymerization was continued for 10 hours at 35–40° C.; initial pressure was 242 psi; final pressure 40 psi. After hydrolysis in boiling water and drying (yield 43 g), a pressed film was tough; IR: C=O absorbency 52%/mil. Inherent viscosity of the hydrolyzed polymer in acetone was 2.37.

EXAMPLE 10

Copolymer of 3-Ketotetrafluoroglutaroyl Fluoride, Hexafluoropropylene and Vinylidene Fluoride

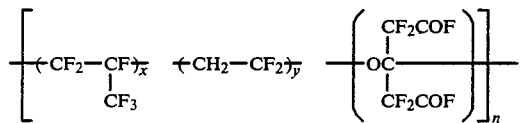

The procedure of Example 4 was repeated using 22 g of $OC(CF_2COF)_2$, 150 g of hexafluoropropene, 26 g of vinylidene fluoride, 0.2 g of perfluoropropionyl peroxide and 150 ml of $Cl_2CFCF_2Cl$ as solvent. Polymerization time, 9 hours at 35° C. Initial pressure: 132 psi; final pressure: 82 psi. After hydrolysis in boiling water and drying, a pressed film was rubbery. Yield 57 g. IR: strong absorption at 2900–3500 cm$^{-1}$ (OH from —COOH); C=O absorbency 30%/mil.

EXAMPLE 11

Copolymer of 3-Ketotetrafluoroglutaric acid (zinc salt) and Vinylidene Fluoride 20 g of 3-ketotetrafluoroglutaric acid/vinylidene fluoride copolymer having neutral equivalent of 1470 and an inherent viscosity in acetone of 0.653 was dissolved at 40° C. in 300 ml of acetone. To the stirred, filtered solution at 25° C., a solution of 2 g of zinc acetate $Zn(O_2CCH_3)_2.2H_2O$ in 40 ml of methanol was added. The solution viscosity increased from water-like to that of mineral oil. The solvent was removed by vacuum evaporation and dried at 100° C.; yield, 15.3 g.

The product was swollen by acetone but not dissolved. A sample was pressed at 190° C. to give a tough, flexible film that after being drawn to four times its length, recovered to a three-fold extension with no further shrinkage. The IR spectrum showed the following differences from that obtained before treatment with zinc acetate. The carbonyl band shifted to 1690 cm$^{-1}$ and a new, broad peak was present at 1570 to 1590 cm$^{-1}$. The sharp OH peak at 3650 cm$^{-1}$ had disappeared and the 3150 cm$^{-1}$ peak was weaker.

Another sample was heated at 190° C. for 2 minutes, then pressed at 1000 psi for 1 minute into yellow-colored test bars and tested in duplicate.

|  | Tensile Strength (psi) | Initial Modulus (psi) | Elongation | |
|---|---|---|---|---|
|  |  |  | (break) (%) | (yield) (%) |
| Base polymer | 3590 | 131,000 | 24 | 17 |
|  | 3698 | 159,000 | 30 | 18 |
| Zn salt | 3431 | 126,000 | 314 | 11 |
|  | 3505 | 112,000 | 172 | 18 |

EXAMPLE 12

Copolymer of 3-Ketotetrafluoroglutaric acid (anilide), Vinylidene Fluoride and Tetrafluoroethylene A copolymer in the acid fluoride form was prepared as described in Example 9, using 44 g of $OC(CF_2COF)_2$, 0.2 g of perfluoropropionyl peroxide, 50 g of vinylidenefluoride, 40 g of tetrafluoroethylene and 100 ml of $Cl_2CFCF_2Cl$ as solvent. The mixture was polymerized at 35° C. for 8 hours. The product (35 g) was washed with $Cl_2CFCF_2Cl$ to remove unreacted ketone, then suspended in 25 ml $Cl_2CFCF_2Cl$. 10 g of aniline was added and the mixture was stored overnight. The pale yellow mixture was filtered, washed with $Cl_2CFCF_2Cl$, then water, and dried. A solution of the product in acetone was filtered; the polymer was reprecipitated by slow addition of the solution to cyclohexane. The product was dried at 110° C. and 0.5 mm pressure for 2 hours (yield, 3 g), and pressed at 190° C. to give a strong, flexible, cold-drawable film that creased without cracking. Its IR spectrum had NH bands at 3420 cm$^{-1}$ and 1610 cm$^{-1}$, a strong C=O band at 1725 cm$^{-1}$ (22 absorbency %/mil). Anal: Nitrogen, 0.58, 0.59%, corresponding to 3.8% by weight of

in the polymer.

I claim:

1. The compound having the formula: $O=C(CF_2COX)_2$ where X is selected from the class consisting of F and Cl.

2. A process for the preparation of the compound $O=C(CF_2COF)_2$ which comprises reacting bis(2-methoxytetrafluoroethyl) ketone with sulfur trioxide, in the presence of methyl 2,2,3,3-tetrafluoro-3-methoxy propionate.

* * * * *